US00PP21880P2

(12) United States Plant Patent
Egger

(10) Patent No.: US PP21,880 P2
(45) Date of Patent: Apr. 19, 2011

(54) ***HEUCHERA* PLANT NAMED 'FIRE CHIEF'**

(50) Latin Name: ***Heuchera* hybrid**
Varietal Denomination: Fire Chief

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 67 days.

(21) Appl. No.: 12/653,630

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell
(74) *Attorney, Agent, or Firm* — Klarquist Sparkman, LLP

(57) ABSTRACT

A new and distinct hybrid of *Heuchera* plant characterized by red to deep burgundy medium sized leaves, bicolor red purple and light pink flowers on short flowering stems, a compact habit, excellent vigor, and excellent tolerance to heat and humidity.

1 Drawing Sheet

Botanical denomination: *Heuchera* hybrid.
Variety designation: 'Fire Chief'.

BACKGROUND OF THE INVENTION

The present invention relates to a new and distinct cultivar of *Heuchera* hybrid and given the cultivar name of 'Fire Chief'. *Heuchera* is in the family Saxifragaceae. *Heuchera* 'Fire Chief' originated from a planned breeding cross between *Heuchera* 834-7, a proprietary unreleased plant, as the seed parent, and *Heuchera* 766-4, a proprietary unreleased plant, as the pollen parent. Compared to the seed parent the new cultivar has darker foliage and a light rather than a heavy veil. Compared to the pollen parent the new cultivar has a lighter veil and red rather than purple black leaves. Compared to *Heuchera* 'Peach Flambé' (U.S. Plant Pat. No. 17,195), the new cultivar has red purple foliage tones rather than peach amber. There are no comparable foliage color *Heuchera* on the market.

This new *Heuchera* is distinguished by:

1. red to deep burgundy medium sized leaves,
2. bicolor red purple and light pink flowers on short flowering stems,
3. a compact habit,
4. excellent vigor,
5. and excellent tolerance to heat and humidity.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one-year-old plant of *Heuchera* 'Fire Chief' growing in the ground in full sun in the garden in May in Canby, Oreg.

FIG. 2 is a two-year-old plant growing in the garden in full sun in October in Canby, Oreg.

DETAILED PLANT DESCRIPTION

The following is a detailed description of the new *Heuchera* cultivar based on observations taken in May of a nine-month-old specimen grown in a one gallon container in a cool greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5th edition.

Plant:

*Form.*—Basal rosette, herbaceous perennial.
*Hardiness.*—USDA Zone 4 to 9.
*Size.*—17 cm tall from top of the foliage to the ground and 40 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Rosette.
*Shape.*—Broadly ovate.
*Lobing/division.*—5 shallow lobes, each with secondary lobes, the terminal is the longest.
*Venation.*—Palmate.
*Margins.*—Crenate.
*Apex.*—Mucronulate.
*Base.*—Cordate, lobes overlapping at the base.
*Blade size.*—Grows to 13 cm long and 11 cm wide.
*Surface texture.*—Glandular on both sides.
*Petiole description.*—4 cm to 13 cm long and 2 mm wide, glandular hairs, Greyed Purple 187B.
*Leaf color.*—Variable depending amount of light, temperature, and age of the leaf; spring new growth topside Greyed Purple 185A, bottom side Greyed Purple 187C; mature leaves Greyed Purple 187B, bottom side Greyed Purple 187B; winter topside is dull red, between Greyed Red 178A and Greyed Purple 185A.

Inflorescence:

*Size.*—Grows to 7 cm long and 4 cm wide.

*Type.*—Thyrse.

*Number of flowers per thyrse.*—About 75 per thyrse.

*Number of thyrse.*—About 6 in first spring bloom.

*Peduncle.*—Grows to 22 cm tall, 3 mm wide at base, Greyed Purple 187A, glandular hairs, with 1 to 2 leaves (ovate, grow to 4.5 cm long and 4 cm wide, 3 to 5 lobed, broadly crenate, mucronulate, cordate, Greyed Purple 187B and glandular on both sides).

*Pedicel.*—Variable in size, with glandular hairs, Greyed Purple 187A.

*Bloom period.*—Late May to June in Canby, Oreg.

Flower bud:

*Size.*—3 mm wide and 5 mm long.

*Description.*—Glandular puberulent, ovoid.

*Color.*—Red Purple 64B on top half and Red Purple 73B on bottom half.

Flower:

*Type.*—Perfect.

*Shape.*—Campanulate,

*Size.*—7 mm long and 4 mm wide.

*Petal description.*—5 in number, inconspicuous, 2 mm long and 1 mm wide, spatulate, tip obtuse, margin sometimes with 2 small side lobes, glabrous on top side, glandular on bottom side; White 155D on top, and Red Purple 73D on bottom.

*Calyx description.*—Campanulate, 5 mm long and 4 mm wide, with 5 lobes, divided ½ way to the base, glandular hairs on both sides; acute, entire, Red Purple 73D on top half and 71C on bottom half.

*Stamen description.*—5 in number, filaments 4 mm long, Red Purple 73D, anthers 0.5 mm, Orange 24B, pollen none.

*Pistil description.*—1, 2-beaked, 4 mm long, Red Purple 73D overall, ovary 1 mm, style 3 mm long.

*Fragrance.*—None.

*Lastingness.*—Each thyrse blooms for about 2 weeks on the plant.

Fruit:

*Type.*—Two beaked capsules.

*Size.*—3.5 mm deep by 5 mm wide.

*Fertility.*—Good.

*Color.*—Brown 200D.

Seed:

*Shape.*—Linear.

*Size.*—2 mm long.

*Color.*—Black, RHS 202A.

Pest and disease tolerance: Excellent disease resistance to powdery mildew, the common problem of *Heuchera*. Susceptible to *Heuchera* rust and root weevils.

I claim:

1. A new and distinct hybrid of *Heuchera* plant as herein illustrated and described.

* * * * *

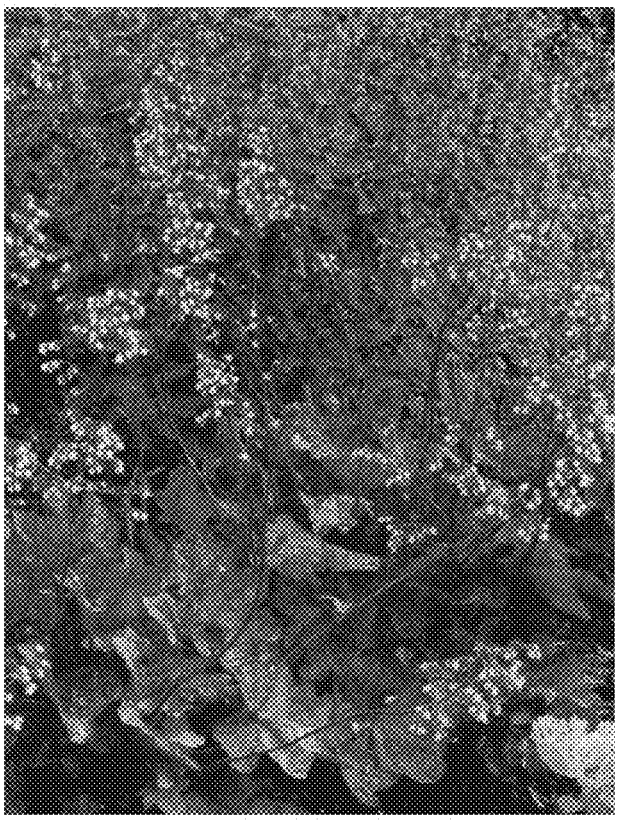

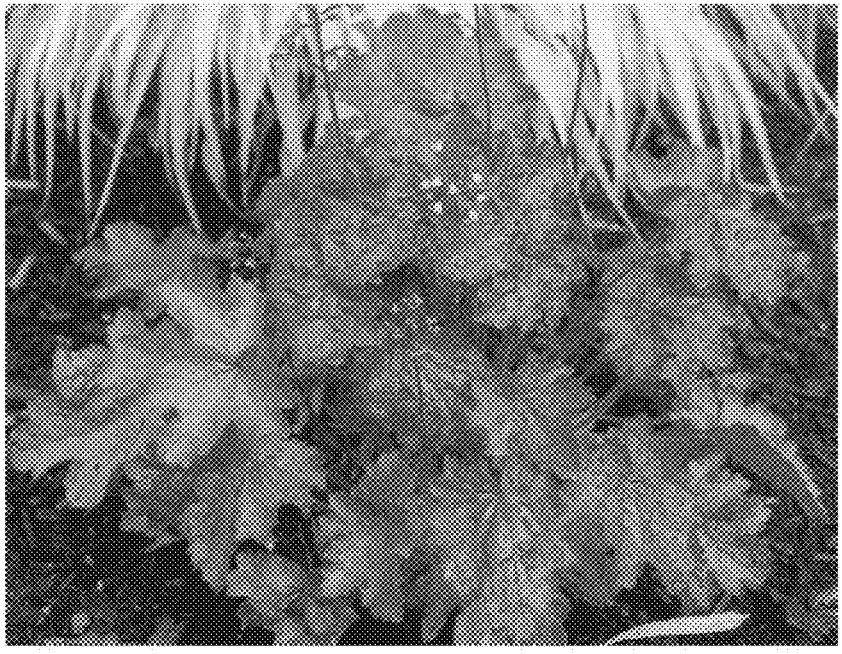
Figure 1 above, Figure 2 below